(12) United States Patent
McGowan et al.

(10) Patent No.: US 6,806,377 B1
(45) Date of Patent: Oct. 19, 2004

(54) PREPARATION OF METALLOCENES CARRYING A CYCLOPENTADIENE COMPRISING A BASIC DONOR GROUP

(75) Inventors: Patrick Columba McGowan, Leeds (GB); Margaret Dymphna McGowan, Leeds (GB)

(73) Assignee: The University of Leeds, Leeds (GB)

( * ) Notice: Subject to any disclaimer, the term of this patent is extended or adjusted under 35 U.S.C. 154(b) by 184 days.

(21) Appl. No.: 10/149,799
(22) PCT Filed: Dec. 13, 2000
(86) PCT No.: PCT/GB00/04760
§ 371 (c)(1),
(2), (4) Date: Oct. 16, 2002
(87) PCT Pub. No.: WO01/42260
PCT Pub. Date: Jun. 14, 2001

(30) Foreign Application Priority Data

Dec. 13, 1999 (GB) ............................................. 9929353

(51) Int. Cl.$^7$ ............................ C07F 17/00; C07F 7/00; B01J 31/00
(52) U.S. Cl. .......................... 556/53; 502/155; 526/943
(58) Field of Search ........................ 556/53; 502/155; 526/943

(56) References Cited

U.S. PATENT DOCUMENTS

| | | | |
|---|---|---|---|
| 2,777,002 A | 1/1957 | Sullivan | ...................... 260/623 |
| 3,920,757 A | 11/1975 | Watson | ................... 260/623 H |
| 4,851,430 A | 7/1989 | Köpf-Maier et al. | ......... 514/502 |
| 5,002,969 A | 3/1991 | Köpf-Maier et al. | ......... 514/492 |
| 6,100,414 A * | 8/2000 | Li et al. | ........................ 556/11 |

FOREIGN PATENT DOCUMENTS

DE        19630580 A1        2/1998

OTHER PUBLICATIONS

Blais et al., "Pendent Aminoalkyl–Substituted Monocyclopentadienyltitanium Compounds and Their Polymerization Behavior," *Organometallics*, 17: 3775–3783 (1998).

Jutzi et al., "Titanium and Zirconium Bent–Sandwich Complexes with the New [2–(Diisopropylamino)ethyl]cycolpentadienyl Ligand: Catalysts for the Polymerization of Ethylene and the Dehydrocoupling of Phenylsilance," *Organometallics* 15: 4153–4161 (1996).

Jutzi et al., "Aminoethyl–Functionalized Cyclopentadienyl Complexes of d–Block Elements," *Eur. J. Inorg. Chem.*, 663–674 (1998).

P. Köpf–Maier, *Antitumor Bis(cyclopentadienyl)metal Complexes: Antitumor Metallocenes*, 261–296.

Toney et al., "Hydrolysis Chemistry of the Metallocene Dichlorides M($\eta^5$–C$_5$H$_5$)$_2$Cl$_2$, M=Ti, V, Zr. Aqueous Kinetics, Equilibria, and Mechanistic Implications for a New Class of Antitumor Agents," *J. Am. Chem. Soc.*, 107: 947–953 (1985).

Herrmann et al., "Cyclische Amine als intramolekulare Hilfsliganden in π–Komplexen des Titans," *Journal of Organometallic Chemistry*, 486:291–295 (1995).

(List continued on next page.)

*Primary Examiner*—Porfirio Nazario-Gonzalez
(74) *Attorney, Agent, or Firm*—Myers Bigel Sibley & Sajovec, PA

(57) ABSTRACT

The invention provides a method for the preparation of a metallocene halide salt having at least one cyclopentadiene group substituted by a basic group, the method comprising reacting together a metal halide with a cyclopentadiene substituted by a basic group. In a preferred embodiment, the substituted cyclopentadiene is substituted with an amino group and the metal halide titanium tetrachloride. The invention provides a single step process for the preparation of metallocene derivatives which are useful in the formulation of medicaments and as polymerisation catalyst precursors.

37 Claims, 2 Drawing Sheets

Figure 1:
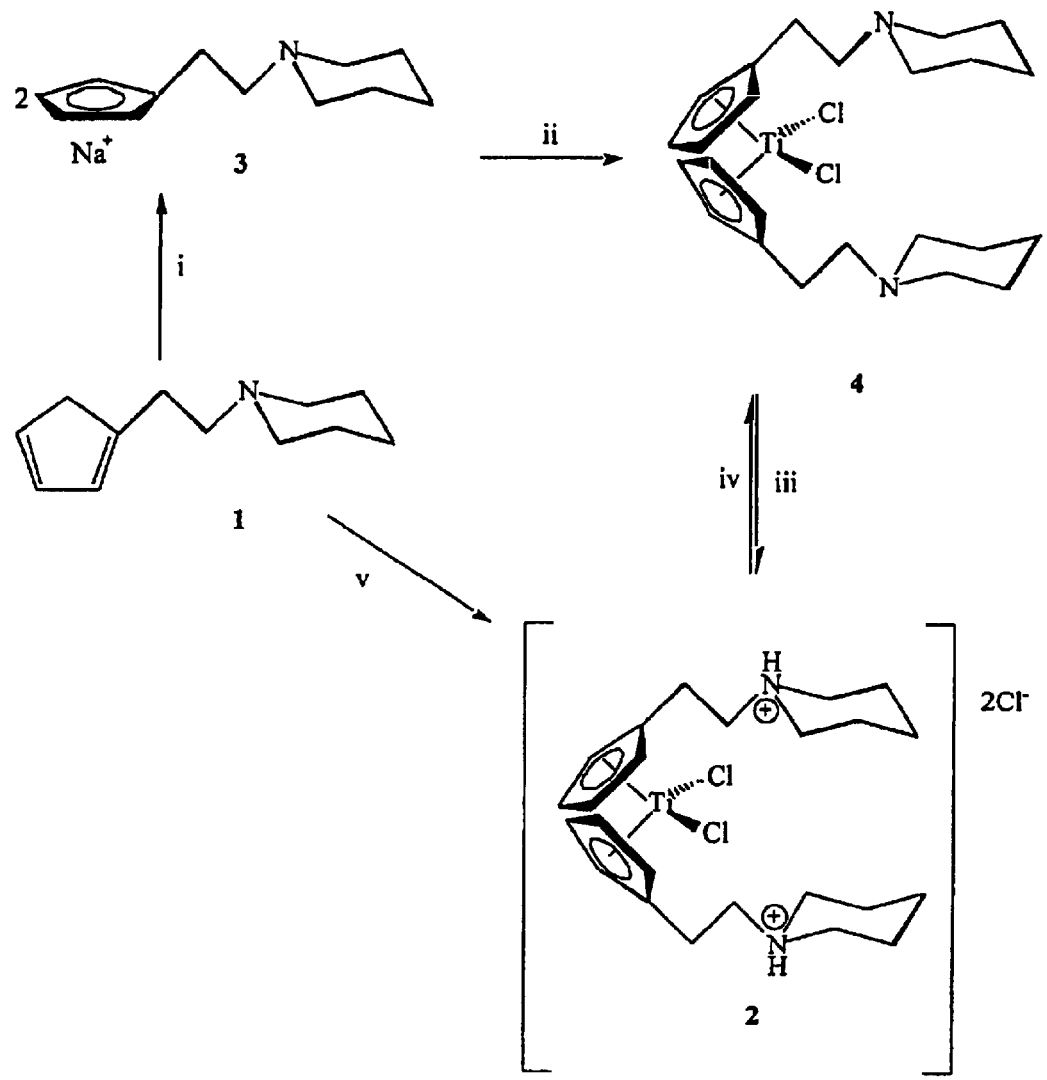

Reagents and conditions: (i) NaH in THF, (ii) TiCl$_4$ in diethyl ether, (iii) HCl, 40% aqueous solution, (iv) MeLi, (v) TiCl$_4$ in toluene, -78°C.

OTHER PUBLICATIONS

Jutzi, P. & Kleimeier, J., "Der (N,N–Dimethylaminoethyl) cyclopentadienyl–Ligand in der Komplexchemie von Titan and Zirkon," *Journal of Organometallic Chemistry*, 486: 287–289 (1995).

Sinnema et al., "Titanium Dichloro, Bis(carbyl), Aryne, and Alkylidene Complexes Stabilized by Linked Cyclopentadienyl–Amido Auxiliary Ligands," *Organometallics*, 16: 4245–4247 (1997).

* cited by examiner

Reagents and conditions: (i) NaH in THF, (ii) TiCl₄ in diethyl ether, (iii) HCl, 40% aqueous solution, (iv) MeLi, (v) TiCl₄ in toluene, -78°C.

Reagents and conditions (i) four equivalents of MeLi in Et$_2$O at -78°C

US 6,806,377 B1

PREPARATION OF METALLOCENES CARRYING A CYCLOPENTADIENE COMPRISING A BASIC DONOR GROUP

RELATED APPLICATIONS

This application claims priority under 35 U.S.C. § 371 from PCT Application No. PCT/GB00/04760, filed in English on Dec. 13, 2000, which claims the benefit of Great Britain Application Serial No. 9929353.2 filed on Dec. 13, 1999, the disclosures of which are incorporated by reference herein in their entireties.

FIELD OF THE INVENTION

This invention relates to methods for the synthesis of metallocenes.

BACKGROUND OF THE INVENTION

Amino-functionalised titanocenes are of increasing interest because of their potential to act as highly active and selective olefin polymerisation catalyst precursors [1,2,3,4]. The neutral amino function can reversibly co-ordinate to the metal centre, potentially stabilising highly reactive intermediates formed during homogeneous catalytic processors. High catalytic activity has been found with group IV metallocenes as well as with metallocenes involving other metals. For instance, half-sandwich complexes of chromium in which the pendant amino function is co-ordinated to the metal centre have been shown to be highly active olefin polymerisation catalysts [5]. Furthermore, the pendant amino function can interact with inorganic support materials, thereby incorporating traditional metallocene catalysts into heterogeneous catalysts.

Quaternisation of the pendant amino group can result in water stable and soluble species [1,2,4]. Such species may not only provide water soluble catalytic compounds but are also useful as anti-tumour drugs having advantages over the known anti-tumour drug titanocene dichloride. Although titanocene dichloride is an efficient anti tumour agent [6,7], it has low solubility and is unstable in aqueous solution. The greater stability and solubility of amino-functionalised titanocenes renders these materials, and their dihydrochloride derivatives, potentially more suitable as anti-tumour agents as well as providing more suitable models for studying the mechanism of action of titanocene dichloride as an anti tumour agent Known synthetic methods for the preparation of the dihydrochloride salts of amino-functionalised titanocenes involve the deprotonation of the neutral cyclopentadiene to give lithium, sodium or thallium salts [2,3,4]. In situ deprotonation can be achieved by the addition of an external base [8]. The reaction of the metal salt with $TiCl_4$ results from the formation of the neutral metallocene which is then reacted with HCl to give the dihydrochloride salt Accordingly such a process involves 3 steps from the cyclopentadiene to the dihydrochloride salt. There is a need for an improved process involving fewer steps and producing the dihydrochloride salt in relatively high yield.

STATEMENTS OF INVENTION

According to the present invention there is provided a method for the preparation of a metallocene halide salt having at least one cyclopentadiene group substituted by a basic group, said method comprising reacting together a metal halide with a cyclopentadiene substituted by said basic group.

Accordingly the present invention provides a single step process for the preparation of an amino-functionalised metallocene which can be produced in high yield. It is believed that this single step process is possible because the method utilises the presence of an "internal base" rather than by making use of an external base in the known 3 step process.

The method of the present invention may be applied to the preparation of metallocenes of both early and late transition metals including the group IV metals Ti, Zr and Hf.

Preferably the metal halide is a homoleptic halide, more preferably a homoleptic chloride, an example being $TiCl_4$.

Preferably the substituted cyclopentadienyl carries a pendant Lewis base. More preferably the Lewis base is provided by an amino group, for instance, a tertiary amino group, examples being —$CH_2CH_2N(CHCH_3)_2$ and —$CH_2CH_2N(CH_2)_5$.

Preferably the cyclopentadienyl is contacted with the metal halide in the presence of an inert solvent such as toluene.

Preferably the substituted cyclopentadiene and the metal halide are reacted together at ambient temperature or below. One reactant may be added to the other in a dropwise fashion. The addition may be carried out more quickly the lower the temperature.

The metallocene halide salt prepared by the method of the present invention may be converted to the neutral metallocene by contacting the salt with a base. Furthermore the metallocene halide salt may be converted to other species. For example, contacting the metallocene halide salt with an alkylating agent results in the formation of an alkyl substituted metallocene.

The method of the present invention represents a new and facile route to metallocene halide salts in high yield. The method is therefore highly advantageous over the known three steps synthetic routes.

DETAILED DESCRIPTION OF THE INVENTION

The present invention will now be described in greater detail and with reference to FIGS. 1 and 2 of the accompanying drawings which illustrate the synthetic routes which will be described.

By way of example, FIG. 1 illustrates the known synthetic route and the method of the present invention for the preparation of an amino-functionalised titanocene; the method of the invention is shown as step (v).

The titanocene dihydrochloride salt 2 can be synthesised either by direct reaction of two equivalents of the neutral cyclopentadiene 1 and $TiCl_4$ in toluene or by reaction of the sodium salt 3 with $TiCl_4$ followed by reaction with HCl. The substituted cyclopentadiene 1 can be synthesised as previously described by Herrmann and co-workers [9]. The dihydrochloride salt is isolated as a dark orange solid which is soluble in a polar solvent such as methanol, water and acetonitrile.

The neutral titanocene 4 can be obtained by reaction of the dihydrochloride 2 with two equivalents of MeLi and by reaction by the sodium salt 3 with T $Cl_4$ in ether. The highly air and moisture sensitive titanocene 4 can be isolated as a crystalline, deep orange solid and is soluble in aprotic, polar and non-polar solvents such as ether and toluene. An analytically pure sample can be obtained by recrystallisation from ether.

Figure 2:
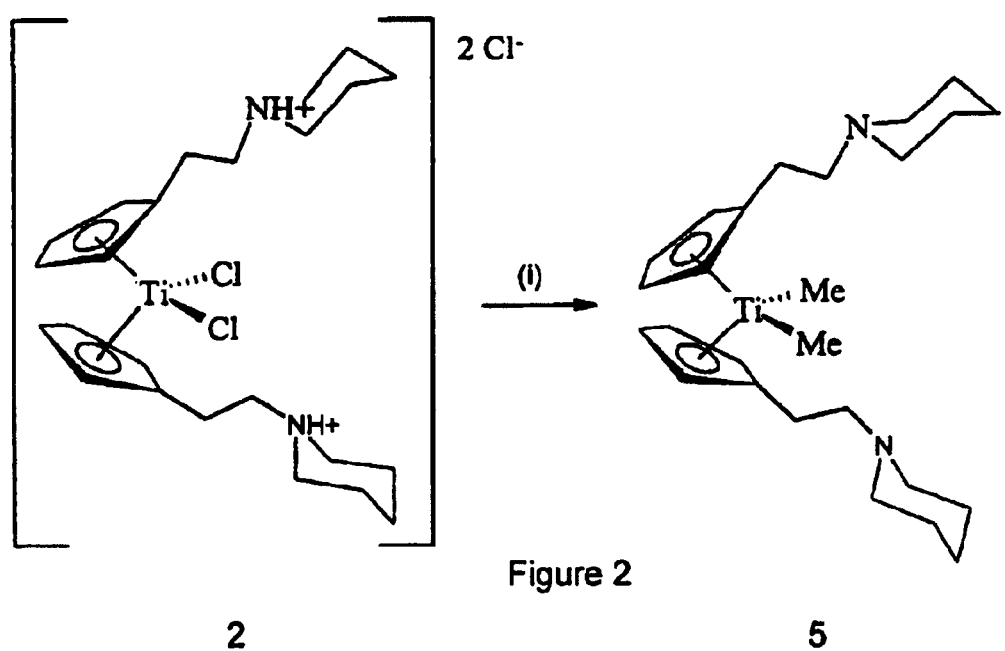

Reaction of the dihydrochloride 2 with four equivalents of MeLi results in the formation of the thermally stable dimethylated species 5, as illustrated in FIG. 2. Species 5 is a highly air sensitive red oil.

Accordingly the present invention provides a synthetic route for a titanocene dihydrochloride which is both air stable and water soluble and avoids a number of synthetic steps in which the reagents are air and water sensitive. The resultant "protected" titanocene can be stored indefinitely and the neutral titanocene can be generated by reaction with a base. Deprotonation can be carried out in situ by a cocatalyst such as MAO (methylalumunoxane) to give the neutral metallocene dichloride as the catalyst precursor. Furthermore, reaction with four equivalents of an alkylating agent generates the dialkyl substituted titanocene.

SPECIFIC EXAMPLES

Examples of the preparation of titanocene compounds will now be described.

Synthesis of $(CpCH_2CH_2N(CH_2)_2(CH_2)_2)_2TiCl_2$ (1)

Method 1: From $NaCpCH_2CH_2N(CH_2)_2(CH_2)_2$ and $TiCl_4$ 1.37 g (0.0069 mol) of $NaCpCH_2CH_2N(CH_2)_2(CH_2)_2$ was added as a slurry in 100 ml of THF to 0.38 ml (0.66 g, 0.0034 mol) $TiCl_4$ in 75 ml of THF. On addition an orange colour developed in the toluene and a colourless precipitate formed. The reaction mixture was left to stir for 1 h after which the solvent was removed in vacuo. The product was extracted in 100 ml of toluene. Recrystallisation from toluene affords the product as dark orange crystals.

Method 2: From $(CpCH_2CH_2N(CH_2)_2(CH_2)_2)_2TiCl_2\cdot 2HCl$

Two equivalents of MeLi (0.0018 mol, 1.26 ml, 1.4M solution in $Et_2O$ were added dropwise to a suspension 0.48 g of $(CpCH_2CH_2N(CH_2)_2(CH_2)_2)_2TiCl_2\cdot 2HCl$ (0.00088 mol) in 100 ml of toluene. The mixture was stirred for 2 h after which an orange colour had developed in the toluene. The solution was filtered and the solvent removed in vacuo. The residue was extracted in 50 ml of toluene and the solvent was removed in vacuo leaving 1 as a dark orange solid. $^1H$ NMR ($C_6D_6$): δ 2.54 (t, 4H, $CpCH_2$), δ 2.07 (t, 4H, $CpCH_2CH_2$), δ 2.3689 (m, 8H, $N(CH_2)_2$) δ 1.55 (m, 8H, $N(CH_2)_2(CH_2)_2$), δ 1.37 (M, 4H, $N(CH_2)_2(CH_2)_2(CH_2)$, 6.26, 5.89 (pt, 8H, CpH). $^{13}C$ NMR ($C_6D_6$): δ 29.16 ($CpCH_2$), δ 59.6 ($CpCH_2CH_2$), δ 55.10 ($N(CH_2)_2$, δ 26.74 ($N(CH_2)_2(CH_2)_2$), δ 25.16 ($N(CH)_2(CH_2)_2(CH_2)$, δ 114.98, 123.31 (Cp ring C, δ 136.65 (Cp ring quaternary). Anal. Calcd for $(CpCH_2CH_2N(CH_2)_2(CH_2)_2)_2TiCl_2$ (449.32); C, 61.16; H, 7.70; N, 5.94. Found: C, 61.4; H, 7.85; N, 6.10.

Synthesis of $(CpCH_2CH_2N(CH_2)_2(CH_2)_2)_2TiCl_2\cdot 2HCl$ (2)

Method 1 (Illustrative of the Method of the Invention): from $TiCl_4$ and $HCpCH_2CH_2N(CH_2)_2(CH_2)_2$ Two equivalents of freshly distilled HCp $CH_2CH_2N(CH_2)_2(CH_2)_2$ (3.0 g, 0.0169 mol) in toluene (50 ml) were added dropwise to a solution of $TiCl_4$ (1.6 g, 0.0085 mol) in toluene (150 ml) at −78° C. The solution was stirred for 30 minutes during which time a dark orange solid had precipitated. The mixture was warmed to room temperature and stirred for an additional 4 h. The toluene was removed in vacuo and the solid was washed with ether and dried in vacuo leaving 2 as a dark orange solid.

Yield=4.1 g, 89%.

Method 2: from $(CpCH_2CH_2N(CH_2)N(CH_2)_2)_2TiCl_2$ and HCl

To a solution of 0.10 g of 1 (in deuterated benzene in an NMR tube) was added an excess of HCl (40% solution. Immediately a dark orange solid precipitated. The benzene was removed in vacuo and the solid was dissolved in $CD_3N$.

$^1H$ NMR MeOD): $^1H$ NMR ($C_6D_6$): δ 3.31 (t, 4H, $CpCH_2$), δ 3.45 (t, 4H, Cp $CH_2CH_2$), δ 3.61, 3.00 (m, 8H, N $(CH_2)_2$) δ 1.95, 1.87 (m, 8H, $N(CH_2)_2(CH_2)_2$), δ 1.54 (m, 4H, $N(CH_2)_2(CH_2)_2CH_2$), 6.72, 6.48 (pt, 8H, CpH). $^{13}C$ NMR ($C_6D_6$): δ 26.43 ($CpCH_2$), δ 57.10 ($CpCH_2CH_2$), δ 54.39 ($N(CH_2)_2$) δ 24.23 ($N(CH_2)_2(CH_2)_2$), δ 22.64 ($N(CH_2)_2(CH_2)_2CH_2$), δ 124.64, 116.95 (Cp ring C), δ 133.33 (Cp ring quaternary). MS (FAB; m/z (relative intensity, %): 472 ($[CpCH_2CH_2NH(CH_2)_2(CH_2)_2)_2TiCl_2]^+$, 7.43).

Synthesis of $(Cp(CH_2)_2N(CH_2)_5)_2TiMe_2$ (3)

To a suspension of 2 in $Et_2O$ (0.5 g, 0.92 mmol, 50 ml $Et_2O$) was added two equivalents of MeLi (1.4 M, 1.3 ml, 1.84 mmol) in $Et_2O$ with vigorous stirring. Evolution of a gas was immediately apparent. The mixture was left to stir at room temperature for 2 h, during which a deep orange solution had formed and a colourless solid precipitated. The $Et_2O$ was removed in vacuo and the product was extracted in toluene to leave the product as a dark red-brown oil.

Synthesis of $[(Cp\ CH_2CH_2N(Me)(CH_2)_2(CH_2)_2)_2\ TiCl_2]\ Cl^-_2$ (4)

Two equivalents (0.19 g, 0.0013 mol) of methyl iodide were added to 0.30 g (0.00067 mol) of $CpCH_2CH_2N(CH_2)_2(CH_2)_2)_2TiCl_2$ in 50 ml of toluene. The reaction mixture was stirred for 30 minutes after which a bright orange precipitate had formed and no colour remained in the toluene. The toluene was filtered from the product which was washed with diethyl ether to leave 4 as a powder red solid.

$^1H$ NMR (MeOD): $^1H$ NMR ($C_6D6$): δ 3.31 (t, 4H, $CpCH_2$), δ 3.45 (t, 4H, Cp $CH_2CH_2$), δ 3.61, 3.00 (m, 8H, N $(CH_2)_2$) δ 1.95, 1.87 (m, 8H, $N(CH_2)_2(CH_2)_2$), δ 1.54 (m, 4H, $N(CH_2)_2(CH_2)_2CH_2$), 6.72, 6.48 (pt, 8H, CpH). $^{13}C$ NMR ($C_6D_6$): δ 26.43 ($CpCH_2$), δ 57.10 ($CpCH_2CH_2$), δ 54.39 ($N(CH_2)_2$) δ 24.23 ($N(CH_2)_2(CH_2)_2$), δ 22.64 ($N(CH_2)_2(CH_2)_2CH_2$), δ 124.64, 116.95 (Cp ring C), δ 133.33 (Cp ring quaternary). MS (FAB; m/z (relative intensity, %): 472 ($[CpCH_2CH_2NH(CH_2)_2(CH_2)_2)_2TiCl_2]^+$, 7.43).

Synthesis of $(Cp(CH_2)_2N(CH_2)_5)_2TiMe_2$ (3)

To a suspension of 2 in $Et_2O$ (0.5 g, 0.92 mmol, 50 ml $Et_2O$) was added two equivalents of MeLi (1.4 M, 1.3 ml, 1.84 mmol) in $Et_2O$ with vigorous sting. Evolution of a gas was immediately apparent The mixture was left to stir at room temperature for 2 h, during which a deep orange solution had formed and a colourless solid precipitated. The $Et_2O$ was removed in vacuo and the product was extracted in toluene to leave the product as a dark red-brown oil.

Synthesis of $[(Cp\ CH_2CH_2N(Me)(CH_2)_2(CH_2)_2)_2\ TiCl_2]Cl^-_2$ (4)

Two equivalents (0.19 g, 0.0013 mol) of methyl iodide were added to 0.30 g (0.00067 mol) of $CpCH_2CH_2N(CH_2)_2(CH_2)_2)_2TiCl_2$ in 50 ml of toluene. The reaction mixture was stirred for 30 minutes after which a bright orange precipitate had formed and no colour remained in the toluene. The toluene was filtered from the product which was washed with diethyl ether to leave 4 as a powder red solid.

Synthesis of $(CpCH(CH_2)_2(CH_2)_2NCH_3)_2TiCl_2$ (5)

Analogous to the preparation of $(CpCH_2CH_2N(CH_2)_2(CH_2)_2)_2TiCl_2$, the sodium salt $NaCpCH(CH_2)_2(CH_2)_2NCH_3$ (0.73 g, 3.92 mmol in 50 ml of THF) was added to a solution of $TiCl_4$ (0.38 g, 1.96 mmol in 100 ml of THF). The mixture was stirred for 2 hours after which a brown precipitate had formed and the solution had turned a deep red colour. The solution was filtered and solvent removed under vacuum to leave a dark orange solid Synthesis of $(CpCH(CH_2)_2(CH_2)_2NCH_3)_2$ $TiCl_2 \cdot 2HCl$ (6)

Analogous to the preparation of $(CpCH_2CH_2N(CH_2)_2(CH_2)_2)_2TiCl_2 \cdot 2HCl$, the product can be synthesised by the direct reaction of $NaCpCH(CH_2)_2(CH)_2NCH_3$ and $TiCl_4$ in toluene and by reaction of $(CpCH(CH_2)_2(CH_2)_2NCH_3TiCl_2$ with HCl.

Selected NMR Data

| Compound | Chemical Shifts of Cyclopentadienyl Protons ($\delta$, ppm) | Solvent |
|---|---|---|
| 1 | 6.26, 5.88 | $C_6D_6$ |
| 2 | 6.68, 6.56 | $CD_3CN$ |
|   | 6.72, 6.48 | $CD_3OD$ |
|   | 6.57, 6.47 | $D_2O$ |
| 3 | 5.53, 5.87 | $C_6D_6$ |
| 4 | 6.75, 6.59 | $CD_3CN$ |
| 5 | 6.37, 6.25 | $CDCl_3$ |
| 6 | 6.75, 6.70 | $CD_3OD$ |

References:
(1) Jutzi, P.; Redeker, T. *Eur. J. Inorg. Chem.* 1998, 663–674.
(2) Jutzi, P.; Redeker, T.; Neumann, B.; Stammler, H.-G. *Organometallics* 1996, 15, 4153–4161.
(3) Blais, M. S.; Chien, J. C. W.; Rausch, M. D. *Organometallics* 1998, 17, 3775–3783.
(4) Jutzi, P.; Kleimeier, J. *J. Organomet. Chem.* 1995, 486, 287–289.
(5) Jolly, P.; Ionas, K.; Verkovnic, G. P. I. German Parent 19630580 A1, 1998
(6) Kopf-Maier, P. In *Complexes in Cancer Chemotherapy*; Keppler, B. K., Kd.; VCH: Weinheim, N.Y., 1993; pp 259.
(7) Toney, J. H.; Marks, T. J. *J. Am. Chem. Soc.* 1885, 107, 947–953.
(8) Sinnema, P.-J.; van der Veen, L.; Spek, A. L.; Veldman, N.; Tauben, J. H. *Organometallics* 1997, 16, 4245–4247.
(9) Herrmann, W. A.; Morawietz, T. P.; Mashima, K. *J. Organomet. Chem.* 1995, 486, 291–295.

What is claimed is:

1. A method for the preparation of a metallocene halide salt having at least one cyclopentadiene group substituted by a basic group, said method comprising reacting together a metal halide with a cyclopentadiene substituted by said basic group.

2. A method as claimed in claim 1 wherein said metal halide is a halide of an early or a late transition metal.

3. A method as claimed in claim 2 wherein said metal comprises titanium, zirconium or hafnium.

4. A method in claim 1 wherein said metal halide comprises a homoleptic halide.

5. A method as claimed in claim 4 wherein said homoleptic halide comprises a homoleptic chloride.

6. A method as claimed in claim 5 wherein said homoleptic chloride comprises titanium tetrachloride.

7. A method as claimed in claim 1 wherein said substituted cyclopentadiene carries a pendant Lewis base.

8. A method as claimed in claim 7 wherein said Lewis base is provided by an amino group.

9. A method as claimed in claim 8 wherein said amino group comprises a tertiary amino group.

10. A method as claimed in claim 9 wherein said tertiary amino group comprises $—CH_2CH_2N(CHCH_3)_2$, or $—CH_2CH_2N(CH_2)_5$.

11. A method as claimed in claim 1 wherein said substituted cyclopentadiene is contacted with said metal halide in the presence of an inert solvent.

12. A method as claimed in claim 11 wherein said inert solvent comprises toluene.

13. A method as claimed in claim 1 wherein said substituted cyclopentadiene and said metal halide are reacted together at ambient temperature or below.

14. A method for the preparation of a metallocene halide salt having at least one cyclopentadiene group substituted by a basic group, said method comprising reacting together a homoleptic halide with a cyclopentadiene substituted by said basic group.

15. A method as claimed in claim 14 wherein said metal halide is a halide of an early or a late transition metal.

16. A method as claimed in claim 15 wherein said metal comprises titanium, zirconium or hafnium.

17. A method as claimed in claim 14 wherein said homoleptic halide comprises a homoleptic chloride.

18. A method as claimed in claim 17 wherein said homoleptic chloride comprises titanium tetrachloride.

19. A method as claimed in claim 14 wherein said substituted cyclopentadiene carries a pendant Lewis base.

20. A method as claimed in claim 19 wherein said Lewis base is provided by an amino group.

21. A method as claimed in claim 20 wherein said amino group comprises a tertiary amino group.

22. A method as claimed in claim 21 wherein said tertiary amino group comprises $—CH_2CH_2N(CHCH_3)_2$, or $—CH_2CH_2N(CH_2)_5$.

23. A method as claimed in claim 14 wherein said substituted cyclopentadiene is contacted with said homoleptic halide in the presence of an inert solvent.

24. A method as claimed in claim 23 wherein said inert solvent comprises toluene.

25. A method as claimed in claim 14 wherein said substituted cyclopentadiene and said homoleptice halide are reacted together at ambient temperature or below.

26. A method for the preparation of a metallocene halide salt having at least one cyclopentadiene group substituted by a basic group, said method comprising reacting together a metal halide with a cyclopentadiene substituted by said basic group, wherein said substituted cyclopentadiene carries a pendant Lewis base.

27. A method as claimed in claim 26 wherein said metal halide is a halide of an early or a late transition metal.

28. A method as claimed in claim 27 wherein said metal comprises titanium, zirconium or hafnium.

29. A method as claimed in claim 26 wherein said metal halide comprises a homoleptic halide.

30. A method as claimed in claim 29 wherein said homoleptic halide comprises a homoleptic chloride.

31. A method as claimed in claim 30 wherein said homoleptic chloride comprises titanium tetrachloride.

32. A method as claimed in claim 26 wherein said Lewis base is provided by an amino group.

33. A method as claimed in claim 32 wherein said amino group comprises a tertiary amino group.

34. A method as claimed in claim 33 wherein said tertiary amino group comprises $—CH_2CH_2N(CHCH_3)_2$, or $—CH_2CH_2N(CH_2)_5$.

35. A method as claimed in claim 26 wherein said substituted cyclopentadiene is contacted with said metal halide in the presence of an inert solvent.

36. A method as claimed in claim 35 wherein said inert solvent comprises toluene.

37. A method as claimed in claim 26 wherein said substituted cyclopentadiene and said metal halide are reacted together at ambient temperature or below.

* * * * *